US012558190B2

(12) United States Patent
Chen

(10) Patent No.: US 12,558,190 B2
(45) Date of Patent: Feb. 24, 2026

(54) MULTIFUNCTIONAL PREOPERATIVE PRECISE LOCATOR SUITABLE FOR MULTIPLE ORGANS

(71) Applicants: Beijing Institute for Cancer Research, Beijing (CN); Peking University Cancer Hospital, Beijing (CN)

(72) Inventor: Mailin Chen, Beijing (CN)

(73) Assignees: Beijing Institute for Cancer Research, Beijing (CN); Peking University Cancer Hospital, Beijing (CN)

( * ) Notice: Subject to any disclaimer, the term of this patent is extended or adjusted under 35 U.S.C. 154(b) by 92 days.

(21) Appl. No.: 18/632,325

(22) Filed: Apr. 11, 2024

(65) Prior Publication Data

US 2025/0082430 A1 Mar. 13, 2025

(30) Foreign Application Priority Data

Sep. 11, 2023 (CN) .......................... 202311165135.9

(51) Int. Cl.
*A61B 90/00* (2016.01)
*A61B 17/34* (2006.01)
(52) U.S. Cl.
CPC .......... *A61B 90/39* (2016.02); *A61B 17/3468* (2013.01); *A61B 2090/3908* (2016.02); *A61B 2090/3983* (2016.02); *A61B 2090/3987* (2016.02)

(58) Field of Classification Search
CPC . A61B 90/39; A61B 17/3468; A61B 17/3403; A61B 2090/3908; A61B 2090/3983; A61B 2090/3987
See application file for complete search history.

(56) References Cited

U.S. PATENT DOCUMENTS

2012/0226146 A1* 9/2012 Schwartz ............... A61B 90/98
359/871
2020/0015852 A1* 1/2020 Harris .................... A61B 10/04

* cited by examiner

*Primary Examiner* — Brooke Labranche

(57) ABSTRACT

The present invention provides a multifunctional preoperative precise locator suitable for multiple organs, comprising a guiding system and a positioning system. The guiding system includes a guiding needle, a guiding needle handle, scale lines, rubber limiters, sharp needle cores, and blunt needle cores. The present invention enhances the safety and ease of operation of preoperative localization of small nodules in various organs, broadens the range of guidance devices for preoperative localization: ultrasound, CT, PET/ CT, and MRI can all be used, significantly improves the accuracy of localization, can precisely guide the surgical resection range, and maximizes the preservation of residual anatomical structures and functions of organs in patients.

9 Claims, 5 Drawing Sheets 1101          701          801

901          1301          1001

1501

MULTIFUNCTIONAL PREOPERATIVE PRECISE LOCATOR SUITABLE FOR MULTIPLE ORGANS

TECHNICAL FIELD

The present invention belongs to the field of medical technology, specifically a multifunctional preoperative precise locator suitable for multiple organs.

BACKGROUND

With the popularization of nationwide physical examinations and the development of diagnostic equipment, an increasing number of small lesions within the human body are being detected, such as pulmonary nodules, hepatic nodules, early gastrointestinal lesions, etc. This has greatly improved the early diagnosis and treatment of lesions. Alongside, there is a growing number of small lesions that cannot be characterized or require early surgical intervention. Precision surgery aims to thoroughly remove the target lesion while ensuring the integrity of the remaining anatomical structures and maximizing functional volume. Consequently, there is an increasing demand for precise localization before surgery for small nodules. Currently, there are various methods and means for preoperative localization of pulmonary nodules, liver and kidney nodules, gastrointestinal lesions, intracranial lesions, breast tumors, etc. These include CT, ultrasound, or endoscopic imaging guidance, percutaneous, intracavitary, or gastrointestinal approaches, using puncture localization needles, hookwire needles, micro spring rings, indocyanine green fluorescent agents, or dyes such as India ink, methylene blue, or indigo carmine, each with its own advantages and disadvantages. For example, preoperative localization needles for pulmonary nodules cannot avoid vascular injury; indocyanine green fluorescent agents used for preoperative localization of lungs, liver, and gastrointestinal lesions require special and expensive detection equipment; sterile requirements for intraoperative ultrasound localization of hepatic nodules are high; or dyes may cause allergic reactions, have low tolerance times (≤24 h/48 h), and are prone to contamination.

Conventional tower-shaped micro spring rings used for medical embolization have good compatibility with human tissues, are generally not easily dislodged, do not cause obvious irritation symptoms, can exist in human tissues for a long time, and do not have concerns about surgical scheduling time and risks. Due to their high safety, stability, comfort, and tolerance for surgical time, their application in preoperative thoracoscopic pulmonary nodule resection has been increasing in recent years. However, the currently used micro spring rings are tower-shaped, suitable for locating and identifying lung tissue, but not very suitable for fixing or identifying hepatic tissue or gastrointestinal wall. Furthermore, their indications for use are limited to vascular embolization, and there are legal risks associated with their off-label use in lung tissue. Additionally, the needle tips of percutaneous puncture needles under image guidance are sharp, which cannot avoid vascular injury and the occurrence of complications.

In summary, there is currently no medical device available that can be universally applied for percutaneous puncture positioning under preoperative imaging guidance for multiple organ nodules in the lungs, liver, kidneys, gastrointestinal tract, etc. Therefore, the present invention provides a multifunctional preoperative precise locator suitable for multiple organs to address the above issues.

SUMMARY

To solve the aforementioned technical problems, the present invention provides a multifunctional preoperative precise locator suitable for multiple organs. The invention aims to address the issues associated with the current use of micro-spring rings in a tower-shaped form, which are suitable for identifying lung tissue but less effective for fixing or identifying liver tissue, gastrointestinal tract walls, etc. Additionally, the indications for their use are limited to vascular embolization, posing legal risks when used in lung tissue beyond the approved indications. Furthermore, the sharp tips of percutaneous puncture guide needles used under imaging guidance cannot avoid the risk of vascular injury and complications.

The multifunctional preoperative precise locator comprises a guiding system and a positioning system. The guiding system includes a guide needle, a guide needle handle, calibration lines, rubber limiters, sharp needle cores, and blunt needle cores. The tail end of the guide needle is connected to the guide needle handle, and the outer sidewall of the guide needle is equipped with calibration lines. The surface of the guide needle is covered with rubber limiters, and the interior of the guide needle is penetrated by sharp needle cores. The tail end of the sharp needle core is connected to a sharp needle core handle, and the interior of the guide needle is penetrated by blunt needle cores. The tail end of the blunt needle core is connected to a blunt needle core handle.

The positioning system is divided into an empty-core push positioning micro-spring ring system and a solid-core push positioning micro-spring ring system. The empty-core push positioning micro-spring ring system comprises a first micro-spring ring tube, a first push rod buckle, an empty-core push rod, an empty-core push rod handle, a first micro-spring ring, a tail line, and an empty-core semi-push mark. The interior of the guide needle is adaptively connected to the first micro-spring ring tube. The tail end of the first micro-spring ring tube is connected to the first push rod buckle, and the interior of the first micro-spring ring tube is connected to the empty-core push rod. The tail end of the empty-core push rod is connected to the empty-core push rod handle, and the interior of the head end of the first micro-spring ring tube is connected to the first micro-spring ring. The tail end of the first micro-spring ring is connected to the tail line, and the surface of the empty-core push rod is connected to the empty-core semi-push mark. The solid-core push positioning micro-spring ring system comprises a second micro-spring ring tube, a second push rod buckle, a solid-core push rod, a solid-core push rod handle, a second micro-spring ring, and a solid-core semi-push mark. The interior of the guide needle is adaptively connected to the second micro-spring ring tube. The tail end of the second micro-spring ring tube is connected to the second push rod buckle, and the interior of the second micro-spring ring tube is connected to the solid-core push rod. The tail end of the solid-core push rod is connected to the solid-core push rod handle, and the interior of the second micro-spring ring tube is implanted with the second micro-spring ring. The surface of the solid-core push rod is connected to the solid-core semi-push mark.

Preferred embodiments include a guide needle with a blunt sanding structure at the outer sheath tip, a hollow structure, and sharp and blunt needle cores whose surface dimensions are compatible with the inner dimensions of the guide needle.

Additionally, preferred embodiments feature guide needle handles, sharp needle core handles, and blunt needle core handles made of plastic material, with rubber limiters for marking the depth of insertion.

Furthermore, the preferred embodiments involve the internal connection of the guide needle with a second micro-spring ring tube, wherein the tail end of the second micro-spring ring tube is connected to a second push rod buckle, and the internal connection of the second micro-spring ring tube with a solid-core push rod, the tail end of which is connected to a solid-core push rod handle. The second micro-spring ring tube is implanted with a second micro-spring ring internally, and the surface of the solid-core push rod is connected to a solid-core semi-push mark.

The first and second micro-spring ring tubes are preferably hollow structures, with lengths equal to the insertion depth of the guide needle and diameters smaller than the inner diameter of the guide needle.

The first and second micro-spring ring tubes are configured to form a linear structure with the first and second micro-spring rings, respectively.

Moreover, the tail line is preferably of medical-grade sterility and positioned within the hollow push rod, with a length equal to the insertion depth of the first micro-spring ring tube.

The first and second push rod buckles are preferably configured to form an elastic snap-fit structure with the hollow and solid-core push rods, respectively.

Additionally, the head end of the first and second micro-spring ring tubes can be implanted with spindle-shaped micro-spring rings and double-tower micro-spring rings, respectively, with the tail end of the first double-tower micro-spring ring connected to the tail line.

Compared to existing technology, the present invention offers the following beneficial effects:

Enhanced safety and ease of operation in preoperative localization of nodules in various organs.

Expanded applicability of preoperative localization guidance devices, including ultrasound, CT, PET/CT, and MRI.

Improved precision in localization for lung, liver, kidney, gastrointestinal tract, brain, and breast nodules.

Increased precision in guiding surgical resection, maximizing preservation of residual anatomical structures and organ function.

Increased success rate and safety of preoperative localization, reducing patient economic burden and enhancing comfort.

Facilitation and promotion of preoperative imaging-guided precise localization applications, further enhancing surgical precision.

Figures 1, 2, 3, 4, 5:
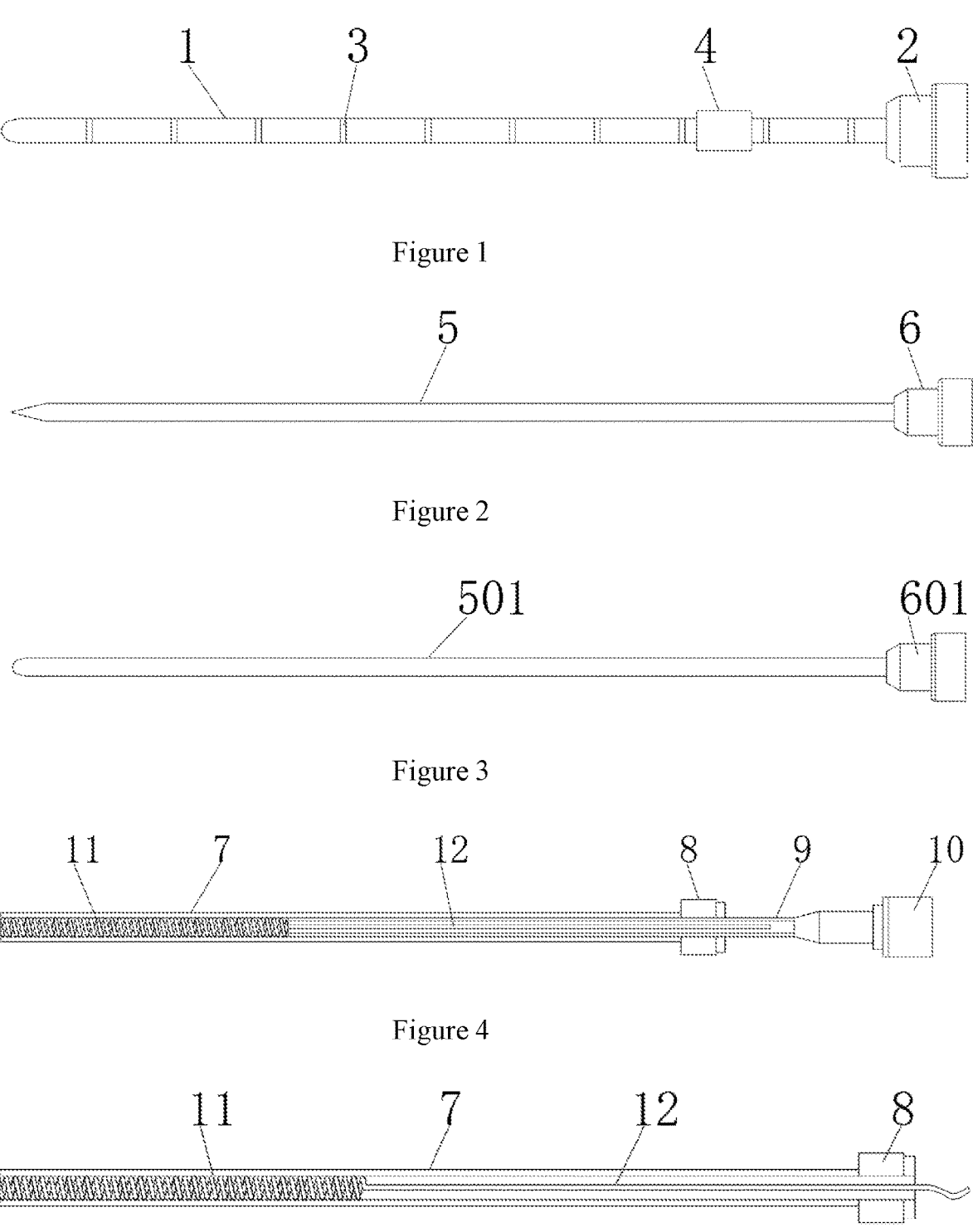
FIG. 1 is a schematic structural diagram of the guide needle of the present invention.
FIG. 2 is a schematic structural diagram of the sharp tip needle core of the present invention.
FIG. 3 is a schematic structural diagram of the blunt tip needle core of the present invention.
FIG. 4 is a schematic structural diagram of the hollow push rod of the present invention.
FIG. 5 is a schematic structural diagram of the first micro spring coil tube of the present invention.
Figure 6:
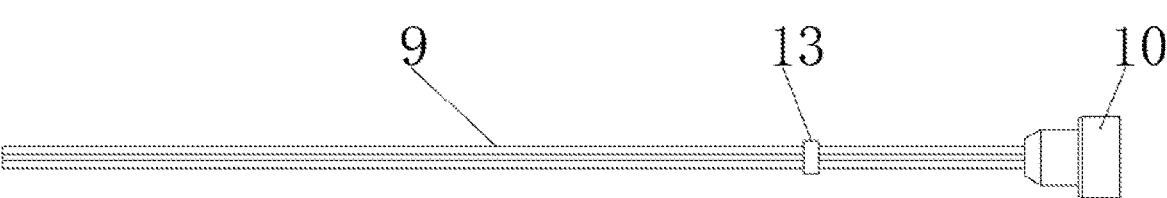
FIG. 6 is a schematic structural diagram of the hollow semi-push mark of the present invention.
Figure 7:
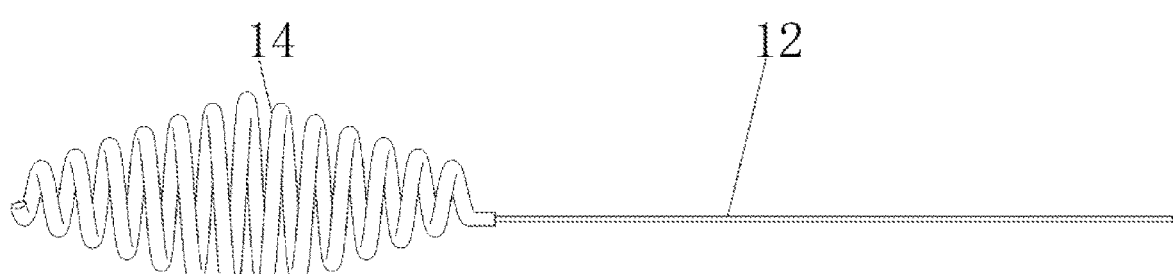
FIG. 7 is a schematic structural diagram of the spindle-shaped micro spring coil of the present invention.
Figure 8:
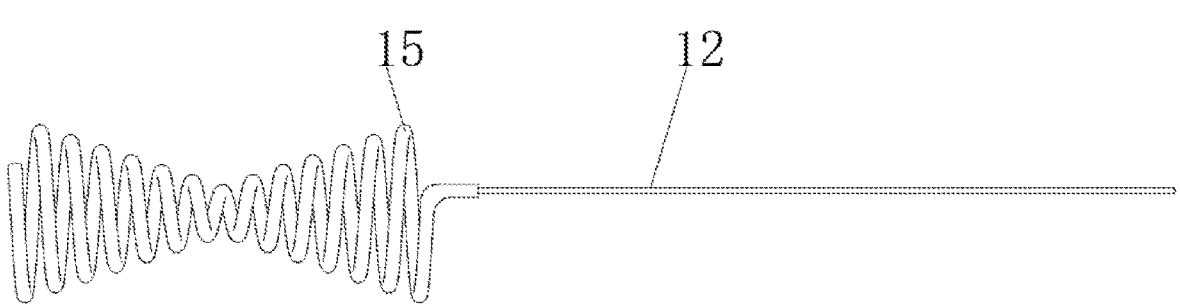
FIG. 8 is a schematic structural diagram of the first twin-tower micro spring coil of the present invention.

wherein, 1. Guide needle; 2. Guide needle handle; 3. Calibration lines; 4. Rubber limiter; 5. Sharp needle core; 501. Blunt needle core; 6. Sharp needle core handle; 601. Blunt needle core handle; 7. First micro-spring ring tube; 701. Second micro-spring ring tube; 8. First push rod buckle; 801. Second push rod buckle; 9. Hollow push rod; 901. Solid-core push rod; 10. Hollow push rod handle; 1001. Solid-core push rod handle; 11. First micro-spring ring; 1101. Second micro-spring ring; 12. Tail line; 13. Hollow push mark; 1301. Solid-core push mark; 14. Spindle-shaped micro-spring ring; 15. First double-tower-shaped micro-spring ring; 1501. Second double-tower-shaped micro-spring ring.

DETAILED DESCRIPTION OF EMBODIMENTS

The embodiments of the present invention will be described in further detail below with reference to the accompanying drawings and examples. The following examples are used to illustrate the invention but are not intended to limit the scope of the invention.

As shown in FIGS. 1-13, the present invention provides a multi-organ multi-functional preoperative precise locator, comprising a guidance system and a positioning system. The guidance system includes a guide needle (1), a guide needle handle (2), calibration lines (3), a rubber limiter (4), a sharp needle core (5), and a blunt needle core (501). The tail end of the guide needle (1) is connected to the guide needle handle (2), and the outer wall of the guide needle (1) is provided with calibration lines (3). The surface of the guide needle (1) is fitted with a rubber limiter (4). The guide needle (1) has a hollow structure, with the sharp needle core (5) passing through its interior, and the blunt needle core (501) also passing through its interior. The sharp needle core (5) is connected to a sharp needle core handle (6), and the blunt needle core (501) is connected to a blunt needle core handle (601).

The positioning system is divided into a hollow push locating micro-spring ring system and a solid-core push locating micro-spring ring system. The hollow push locating micro-spring ring system includes a first micro-spring ring tube (7), a first push rod buckle (8), a hollow push rod (9), a hollow push rod handle (10), a first micro-spring ring (11), a tail line (12), and a hollow push mark (13). The guide needle (1) can be adaptively connected to the first micro-spring ring tube (7). The first micro-spring ring tube (7) is connected to the hollow push rod (9), which in turn is connected to the hollow push rod handle (10). The first micro-spring ring (11) is connected to the head end of the first micro-spring ring tube (7), and the tail end of the first micro-spring ring (11) is connected to the tail line (12). The surface of the hollow push rod (9) is connected to the hollow push mark (13). The solid-core push locating micro-spring ring system includes a second micro-spring ring tube (701), a second push rod buckle (801), a solid-core push rod (901), a solid-core push rod handle (1001), a second micro-spring ring (1101), and a solid-core push mark (1301). The guide needle (1) can be adaptively connected to the second micro-spring ring tube (701).

Referencing FIG. 1, the outer sheath of the guide needle (1) has a blunt sanding structure, and the guide needle (1) is hollow. The surface dimensions of the sharp needle core (5) and the blunt needle core (501) are adapted to the internal dimensions of the guide needle (1).

Referencing FIGS. 1-3, the guide needle handle (2), sharp needle core handle (6), and blunt needle core handle (601) are all made of plastic material, and the rubber limiter (4) can be used to mark the depth of penetration.

Figure 9:
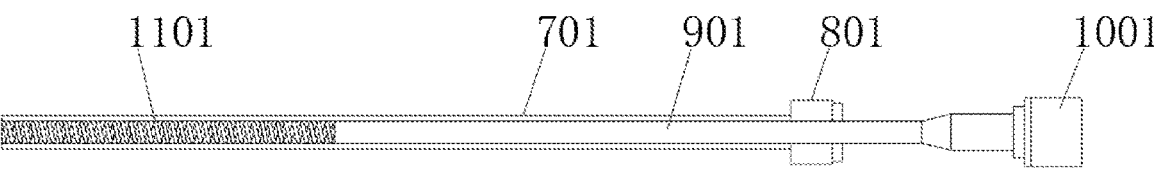
FIG. 9 is a schematic structural diagram of the solid push rod of the present invention.
Figure 10:
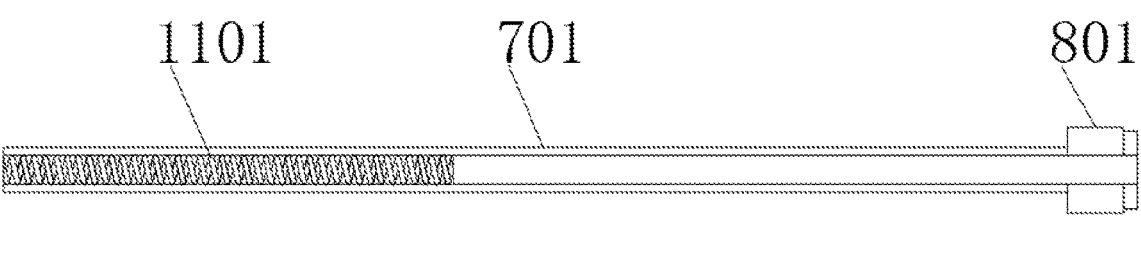
FIG. 10 is a schematic structural diagram of the second micro spring coil tube of the present invention.
Figure 11:
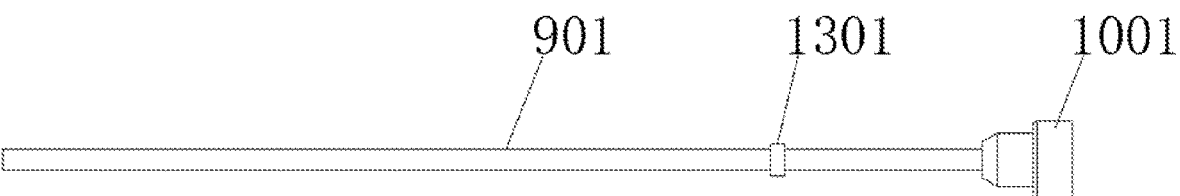
FIG. 11 is a schematic structural diagram of a solid semi-push mark of the present invention.
Figure 12:
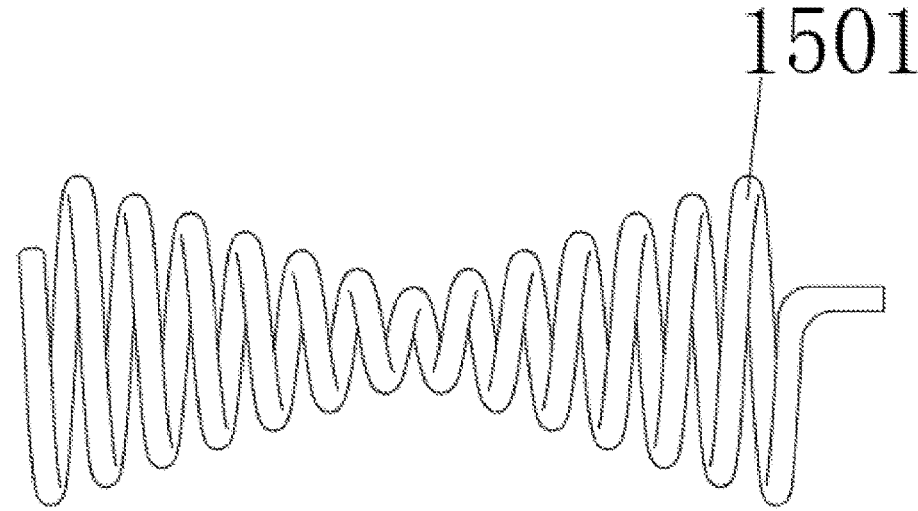
FIG. 12 is a schematic structural diagram of the second twin-tower micro spring coil of the present invention.
Figure 13:
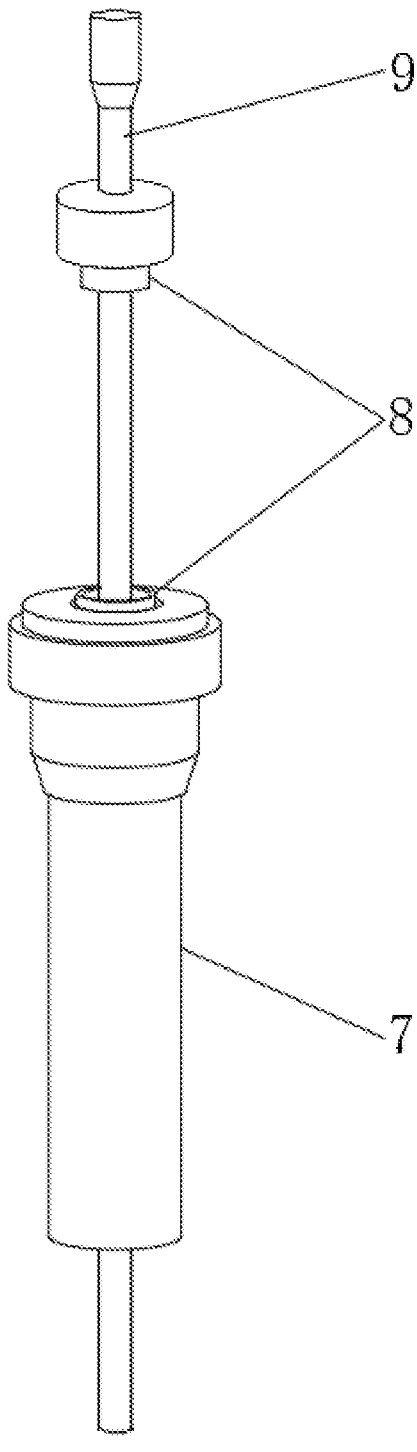
FIG. 13 is a schematic diagram of the push rod buckle decomposed connection structure of the present invention.
Figure 14:
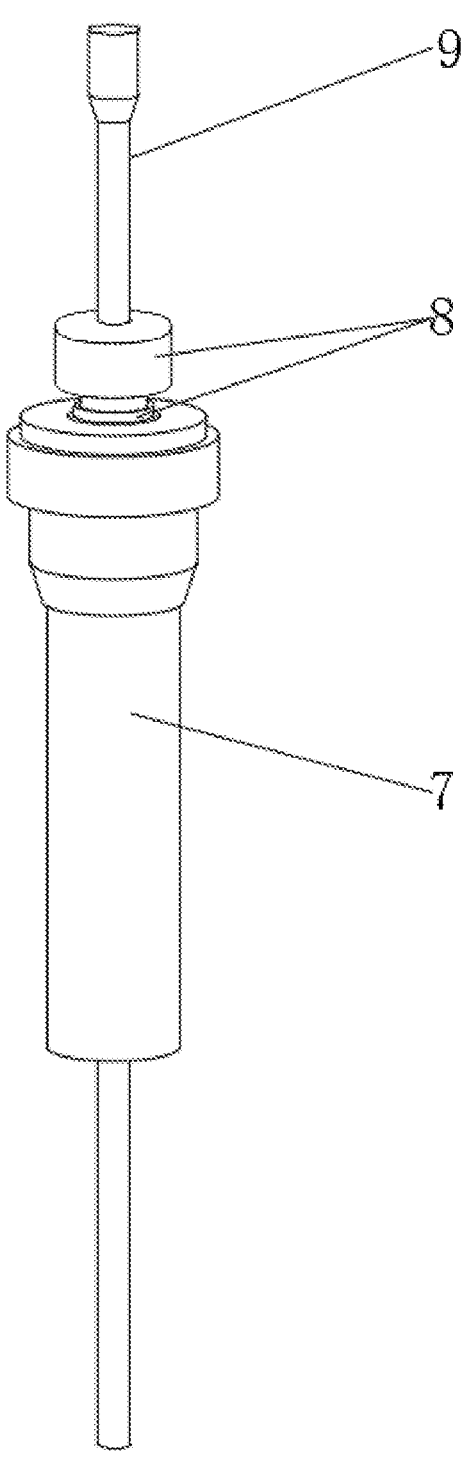
FIG. 14 is a schematic diagram of the snap-fit connection structure of the push rod according to the present invention.

Referring FIG. 9, where the guide needle (1) is internally connected to the second micro-spring ring tube (701), the tail end of which is connected to the second push rod buckle (801). The internal of the second micro-spring ring tube (701) is connected to the solid-core push rod (901), the tail end of which is connected to the solid-core push rod handle (1001). The second micro-spring ring (1101) is implanted inside the second micro-spring ring tube (701), and the surface of the solid-core push rod (901) is connected to the solid-core half-push mark (1301).

Referencing FIG. 9, both the first micro-spring ring tube (7) and the second micro-spring ring tube (701) are hollow structures. Their lengths are such that they align flush with the guide needle (1) after insertion, and their outer diameters are smaller than the inner diameter of the guide needle (1).

Referencing FIG. 9, both the first micro-spring ring tube (7) and the second micro-spring ring tube (701) form a linear structure with the first micro-spring ring (11) and the second micro-spring ring (1101), respectively.

Referencing FIGS. 4-8, the tail line (12) is of medical sterile type and is located inside the hollow push rod (9). The length of the hollow push rod (9) is such that it aligns flush with the head end of the first micro-spring ring tube (7) after complete insertion.

Referencing FIGS. 4-13, both the first push rod buckle (8) and the second push rod buckle (801) form an elastic snap-fit structure with the hollow push rod (9) and the solid-core push rod (901), respectively. When it is necessary to fix the hollow push rod (9), the first push rod buckle (8) is rotated to engage with the hollow push rod (9), causing it to undergo elastic deformation and securely grip the hollow push rod (9) to prevent it from sliding automatically. When it is necessary to push the hollow push rod (9), the first push rod buckle (8) is rotated aside. Throughout this process, the first push rod buckle (8) frictionally contacts the tail end of the first micro-spring ring tube (7) to prevent free rotation.

Referencing FIG. 4-11, both the first micro-spring ring tube (7) and the second micro-spring ring tube (701) can have a spindle-shaped micro-spring ring (14) implanted inside their head ends.

Referencing FIGS. 7-12, both the first micro-spring ring tube (7) and the second micro-spring ring tube (701) can have a first double-tower micro-spring ring (15) and a second double-tower micro-spring ring (1501) implanted inside their head ends, with the tail end of the first double-tower micro-spring ring (15) connected to the tail line (12).

Embodiment 1

Localization of intracranial tumors under MRI guidance: Following a three-dimensional MRI scan of the head and determination of the surgical path by a neurosurgeon, a bone marrow biopsy needle is used to locally drill through the skull along the surgical path. Then, a specialized coaxial puncture guide needle (1) with a sharp needle core (5) is used to penetrate through the layers of meninges and gradually advance into the brain parenchyma. When encountering vascular portions, the sharp needle core (5) is replaced with a blunt needle core (501) to separate them until reaching the vicinity of the intracranial tumor. Subsequently, the needle core is withdrawn, and the first micro-spring ring tube (7) with a spindle-shaped micro-spring ring (14) and tail line (12) is inserted, aligning its head end flush with the guide needle (1) head end. The first push rod buckle (8) is released, the top of the first push rod locking mechanism (8) is matched with the thick rubber stopper at the head end of the first micro spring coil tube (7), while the fine rubber seat at the handle end of the first micro spring coil tube (7) is also matched with the first push rod locking mechanism (8). The hollow push rod (9) is placed inside the first micro spring coil tube (7) to stabilize it. The spindle-shaped micro spring coil (14) used for positioning is pushed out using the hollow push rod (9). A second scan is then performed to confirm the positioning of the first micro spring coil (11) around the tumor. Subsequently, the first micro spring coil tube (7) and guide needle (1) are removed, and the correct positioning of the first micro spring coil (11) and tail thread (12) is verified before completing the procedure.

Embodiment 2

Localization of breast nodules under molybdenum target guidance: Breast nodules can also be localized using breast MRI in axial and oblique positions. After discussing and determining the surgical path with a breast surgeon, a specialized coaxial puncture guide needle (1) with a sharp needle core (5) is used to penetrate the breast skin, subcutaneous fat, and gradually advance into the breast parenchyma. When encountering vascular portions, the sharp needle core (5) is replaced with a blunt needle core (501) to separate them until reaching the vicinity of the breast nodule. Subsequently, the needle core is withdrawn, and the first micro-spring ring tube (7) with a spindle-shaped micro-spring ring (14) and tail line (12) is inserted. The position of the guide needle (1) head end is confirmed by another scan, and then the first push rod buckle (8) is released, the top of the first push rod locking mechanism (8) is matched with the thick rubber stopper at the head end of the first micro spring coil tube (7), while the fine rubber seat at the handle end of the first micro spring coil tube (7) is also matched with the first push rod locking mechanism (8). The hollow push rod (9) is placed inside the first micro spring coil tube (7) to stabilize it. The spindle-shaped micro spring coil (14) is then pushed out. Repeat scanning is performed to confirm the positioning of the first micro spring coil (11) around the tumor. Subsequently, the first micro spring coil tube (7) and guide needle (1) are removed, and the final scan is done to confirm the positioning of the first micro spring coil (11) and tail thread (12), completing the procedure.

Embodiment 3

Localization of pulmonary nodules on lung CT scans: Initially, a comprehensive CT scan of the lungs is conducted to identify the location of pulmonary nodules. According to the requirements of thoracic surgeons, there are two methods of localization: single-line localization or multi-line localization. Single-line localization is mainly used for local wedge resection. It involves marking the skin surface for localization, determining the specific target point of the first microspring coil 11, designing the needle insertion path and depth. A dedicated coaxial puncture-guiding needle 1 with a sharp needle core 5 is used to penetrate the skin, subcutaneous fat, intercostal muscles, and pleura, gradually advancing into the lung parenchyma. After reaching the vicinity of the nodule, the sharp needle is retracted, and an insertion sheath for the first microspring coil 7, which is a spindle-shaped microspring coil 14 with a tail wire 12, is placed. The position of the needle tip is confirmed again by scanning, and then the first push rod latch 8 is released, the top of the first push rod locking mechanism (8) is matched with the thick rubber stopper at the head end of the first micro spring coil tube (7), while the fine rubber seat at the handle end of the first micro spring coil tube (7) is also matched with the first push rod locking mechanism (8). The hollow push rod (9) is placed inside the first micro spring coil tube (7) to stabilize it. The spindle-shaped micro spring coil (14) is then pushed out. Repeat scanning is performed to confirm the positioning of the first micro spring coil (11) around the tumor. Subsequently, the first micro spring coil tube (7) and guide needle (1) are removed, and the final scan is done to confirm the positioning of the first micro spring coil (11) and tail thread (12), completing the procedure. Multiple tail threads can be used for localization in sub-segmental or lobar resections. Discuss with the thoracic surgeon to determine the scope of surgical resection, use multiple first micro spring coils (11) for precise delineation of the resection range of sub-segments or lobes.

Embodiment 4

Localization of hepatic intrahepatic nodules under liver MRI guidance: Liver MR scanning is conducted first to identify the location of hepatic nodules. After discussing with hepatobiliary surgeons to determine the surgical pathway, a dedicated coaxial puncture-guiding needle 1 with a sharp needle core 5 is used to penetrate the skin, subcutaneous fat, and peritoneum, gradually advancing into the liver parenchyma. When encountering vascular portions, the sharp needle core 501 is replaced with a blunt one for separation. The needle is then advanced close to the hepatic nodule. After retracting the needle core, an insertion sheath for the first microspring coil 7, which is a spindle-shaped microspring coil 14 with a tail wire 12, is placed. The position of the needle tip is confirmed again by scanning. The first push rod latch 8 is released to deploy the spindle-shaped microspring coil 14. The position of the first microspring coil 11 around the tumor is confirmed by repeated scanning. Finally, the insertion sheath for the first microspring coil 7 and the guiding needle 1 are removed, and the position of the first microspring coil 11 and the tail wire 12 is confirmed by scanning. Similar localization techniques can also be applied preoperatively to nodules in solid organs such as the kidneys and spleen.

Embodiment 5

Localization of rectosigmoid colon nodules under pelvic CT guidance: A CT scan of the abdomen and pelvis is conducted first to identify the location of colon nodules. According to the surgical approach determined by colorectal surgeons, local anesthesia is administered, and a coaxial puncture-guiding needle 1 is used to puncture along the surgical approach, penetrating the peritoneum into the abdominal cavity. When encountering vascular portions, the sharp needle core 501 is replaced with a blunt one for separation, until reaching near the wall of the colonic nodule. Then, the guiding needle 1 is advanced into the colonic lumen using the sharp needle core 5. The position is confirmed by CT scanning. An insertion sheath for the first microspring coil 7, which is a first double-tower-shaped microspring coil 15 with a tail wire 12, is placed. The first push rod latch 8 is released, and the push rod is pushed to the halfway mark. The CT is observed to ensure that the distal first double-tower-shaped microspring coil 15 pops out into the colonic lumen. The needle and the insertion sheath for the first microspring coil 7 are then withdrawn by about 3 to 8 mm, confirming that the needle tip is located outside the colonic wall. The proximal first double-tower-shaped microspring coil 15 is then pushed out again, ensuring that it is embedded in the colonic wall. Finally, the first microspring coil 7 and the guiding needle 1 are completely removed, and the position of the first double-tower-shaped microspring coil 15 and the tail wire 12 is confirmed by scanning, completing the localization.

Localization and definition of the surgical range of upper and lower edges of ascending colon nodules under abdominal CT guidance: When positioning the puncture guiding needle 1 and the first microspring coil tube 7, which reaches the proximal and distal ends of the localized nodule within the colonic lumen, the solid core push rod 901 is pushed to the halfway mark: the midpoint of the length of the second double-tower-shaped microspring coil 1501. CT observation is conducted to ensure that the distal end of the second double-tower-shaped microspring coil 1501 pops out into the colonic lumen. Then, the guiding needle 1 and the first microspring coil tube 7 are withdrawn together by about 3-8 mm, the thickness of the colonic wall, to confirm that the needle tip is located outside the colonic wall. The proximal end of the second double-tower-shaped microspring coil 1501 is pushed out again to confirm its embedding on the upper and lower edges of the gastrointestinal lesion. Then, the guiding needle 1 and the first microspring coil tube 7 are completely withdrawn, accurately defining the range of upper and lower resection of gastrointestinal lesions.

Specific working principle: As shown in FIGS. 1-12, when using the multifunctional surgical locator applicable to multiple organs, the positioning and guiding system reaches the site of the localized nodule. Sharp needle core 5 and blunt needle core 501 can be replaced during the process. After the guiding system reaches the site, the positioning system is used to accurately locate the surgical site. The process involves pulling out the needle and replacing it with the first microspring coil tube 7. Then, the push rod is used to push the first microspring coil 11 inside the first microspring coil tube 7 for surgical localization. The specific steps are as follows: when the guiding needle 1 and the first microspring coil tube 7 reach the vicinity of the localized nodule, the solid core push rod 9 is used to push the first microspring coil 11 to the position around the nodule. The guiding needle 1 and the first microspring coil tube 7 are withdrawn together, leaving the tail wire 12 outside the tissue for identification by the laparoscope during surgery. For deeper gastrointestinal lesion localization, the first double-tower-shaped microspring coil 15 with a tail wire 12 is used. When the guiding needle 1 and the first microspring coil tube 7 reach the proximal and distal ends of the localized nodule within the colonic lumen, the solid core push rod 9 is used to push to the halfway mark of the first microspring coil 11 length. CT observation is conducted to ensure that the distal end of the first double-tower-shaped microspring coil 15 pops out into the colonic lumen. Then, the guiding needle 1 and the first microspring coil tube 7 are withdrawn together by about 3-8 mm, the thickness of the colonic wall, to confirm that the needle tip is located outside the colonic wall. The first double-tower-shaped microspring coil 15 is then pushed out again, and then the guiding needle 1 and the first microspring coil tube 7 are completely withdrawn, leaving the tail wire 12 embedded in the abdominal wall outside the colon for identification by the laparoscope during surgery. Additionally, there is another solid core push rod positioning microspring coil system that can be used for precise localization of gastrointestinal lesions. The second double-tower-shaped microspring coil 1501 is placed inside the second microspring coil tube 701. When the guiding needle 1 and the second microspring coil tube 701 reach the proximal and distal ends of the localized nodule within the colonic lumen, the solid core push rod 901 is used to push to the halfway mark of the length of the second double-tower-shaped microspring coil 1501. CT observation is conducted to ensure that the distal end of the second double-tower-shaped microspring coil 1501 pops out into the colonic lumen. Then, the guiding needle 1 and the second microspring coil tube 701 are withdrawn together by about 3-8 mm, the thickness of the colonic wall, to confirm that the needle tip is located outside the colonic wall. The proximal end of the second double-tower-shaped microspring coil 1501 is then pushed out again, and then the guiding needle 1 and the second microspring coil tube 701 are completely withdrawn, accurately defining the range of upper and lower resection of gastrointestinal lesions. The guiding needle of the present invention uses a blunt needle core 501, which can avoid damage to intrahepatic vessels and facilitate more accurate localization. It can be used not only for wedge resection of pulmonary nodules but also for localization before subsegmental and segmental lung resection, precise guidance and definition of surgical resection applications in the lungs, liver, kidneys, gastrointestinal tract, brain, breasts, and other areas. It can also be used for preoperative puncture localization of hepatic and gastrointestinal lesions. The microspring coil used for localization replaces traditional metal localization hooks or needles, has good compatibility with human tissues, is generally not easy to fall off, does not cause obvious irritation symptoms, and can exist in lung, liver, and gastrointestinal tissues for a long time without worrying about surgical scheduling time and risks. It is simple and easy to operate, without technical difficulty, and there is no need to worry about falling off or displacement, reducing the patient's foreign body sensation and discomfort, and improving safety and success rate.

In addition, the preoperative puncture precise positioning device can not only be used for puncture positioning under the guidance of ultrasound, CT, PET/CT and other imaging, such as the lungs, liver, gastrointestinal tract, etc., but can also be used under the guidance of magnetic resonance imaging after demagnetization. Preoperative puncture positioning, which also greatly expands its application in the lungs, liver, kidneys, gastrointestinal tract, brain, breast, etc., such as intracranial lesions, etc. This is a multifunctional preoperative precise locator suitable for multiple organs specialty.

The embodiments of the present invention are given for the sake of illustration and description. Although the embodiments of the present invention have been shown and described above, it can be understood that the above-mentioned embodiments are illustrative and should not be construed as limitations of the present invention. Those of ordinary skill in the art can make changes, modifications, replacements and modifications to the above embodiments within the scope of the present invention.

What is claimed is:

1. A multifunctional preoperative precise locator suitable for multiple organs comprises a guiding system and a positioning system; the guiding system includes a guiding needle (1), a guiding needle handle (2), scale lines (3), rubber limiters (4), sharp needle cores (5), and blunt needle cores (501); the tail end of the guiding needle (1) is connected to the guiding needle handle (2), the scale lines (3) are set on the outer wall of the guiding needle (1); the rubber limiters (4) are fitted onto the surface of the guiding needle (1); sharp needle cores (5) pass through the interior of the guiding needle (1), and the tail end of sharp needle core (5) is connected to a sharp needle core handle (6); blunt needle cores (501) also pass through the interior of the guiding needle (1), and the tail end of blunt needle core (501) is connected to a blunt needle core handle (601); the positioning system comprises an empty-core push positioning micro spring ring system and a solid-core push positioning micro spring ring system; the empty-core push positioning micro spring ring system includes a first micro spring ring tube (7), a first push rod buckle (8), an empty-core push rod (9), an empty-core push rod handle (10), a first micro spring ring (11), a tail line (12), and an empty-core semi-push indicator (13); the interior of the guiding needle (1) can be adaptably connected to the first micro spring ring tube (7); the tail end of the first micro spring ring tube (7) is connected to the first push rod buckle (8); the interior of the first micro spring ring tube (7) is connected to the empty-core push rod (9), whose tail end is connected to the empty-core push rod handle (10); the head end of the first micro spring ring tube (7) is internally connected to the first micro spring ring (11), whose tail end is connected to the tail line (12); the surface of the empty-core push rod (9) is connected to the empty-core semi-push indicator (13); the solid-core push positioning micro spring ring system comprises a second micro spring ring tube (701), a second push rod buckle (801), a solid-core push rod (901), a solid-core push rod handle (1001), a second micro spring ring (1101), and a solid-core semi-push indicator (1301); the interior of the guiding needle (1) can be adaptably connected to the second micro spring ring tube (701); the tail end of the second micro spring ring tube (701) is connected to the second push rod buckle (801); the interior of the second micro spring ring tube (701) is connected to the solid-core push rod (901), whose tail end is connected to the solid-core push rod handle (1001); the interior of the second micro spring ring tube (701) is implanted with the second micro spring ring (1101), and the surface of the solid-core push rod (901) is connected to the solid-core semi-push indicator (1301).

2. The multifunctional preoperative precise locator suitable for multiple organs as claimed in claim 1, wherein, the outer sheath of the guiding needle (1) is blunt matte structure at the head end, the guiding needle (1) is hollow, and the surface dimensions of the sharp needle core (5) and the blunt needle core (501) are compatible with the internal dimensions of the guiding needle (1).

3. The multifunctional preoperative precise locator suitable for multiple organs as claimed in claim 1, wherein; the guiding needle handle (2), sharp needle core handle (6), and blunt needle core handle (601) are all made of plastic material, and the rubber limiter (4) can be used to mark the depth of penetration.

4. The multifunctional preoperative precise locator suitable for multiple organs as claimed in claim 1, wherein, the first micro spring ring tube (7) and the second micro spring ring tube (701) are both hollow structures, the lengths of the first micro spring ring tube (7) and the second micro spring ring tube (701) are the same as the length from the rear end to the front end of the guiding needle (1) after the guiding needle (1) is inserted into the first micro spring ring tube (7) and the second micro spring ring tube (701), and the outer diameter of the first micro spring ring tube (7) and the second micro spring ring tube (701) is smaller than the inner diameter of the guiding needle (1).

5. The multifunctional preoperative precise locator suitable for multiple organs as claimed in claim 1, wherein, the first micro spring ring tube (7) and the second micro spring ring tube (701) respectively form straight-line structures with the first micro spring ring (11) and the second micro spring ring (1101).

6. The multifunctional preoperative precise locator suitable for multiple organs as claimed in claim 1, wherein the tail line (12) is located inside the hollow core push rod (9), wherein the length of the hollow core push rod (9) is equal to the length from the rear end to the front end of the first micro spring ring tube (7) after the hollow core push rod (9)

is fully inserted to the first micro spring ring tube (7), and is flush with the front end of the first micro spring ring tube (7).

7. The multifunctional preoperative precise locator suitable for multiple organs as claimed in claim 1, wherein, the first push rod buckle (8) and the second push rod buckle (801) respectively form an elastic engagement structure with the hollow core push rod (9) and the solid core push rod (901).

8. The multifunctional preoperative precise locator suitable for multiple organs as claimed in claim 1, wherein, the front end of the first micro spring ring tube (7) and the second micro spring ring tube (701) can be respectively implanted with spindle-shaped micro spring rings (14).

9. The multifunctional preoperative precise locator suitable for multiple organs as claimed in claim 1, wherein, the front end of the first micro spring ring tube (7) and the second micro spring ring tube (701) can be respectively implanted with the first double-tower micro spring ring (15) and the second double-tower micro spring ring (1501), wherein the tail end of the first double-tower micro spring ring (15) is connected to the tail line (12).

*  *  *  *  *